US00PP26048P3

(12) United States Plant Patent
Van Dijk

(10) Patent No.: US PP26,048 P3
(45) Date of Patent: Nov. 3, 2015

(54) *ANTHURIUM* PLANT NAMED 'ANTHDINWAQ'

(50) Latin Name: ***Anthurium andreanum* L.**
Varietal Denomination: ANTHDINWAQ

(71) Applicant: ANTHURA B.V., Bleiswijk (NL)

(72) Inventor: Jan Van Dijk, Bleiswijk (NL)

(73) Assignee: ANTHURA B.V., Bleiswijk (NL)

( * ) Notice: Subject to any disclaimer, the term of this patent is extended or adjusted under 35 U.S.C. 154(b) by 166 days.

(21) Appl. No.: 13/998,360

(22) Filed: Oct. 24, 2013

(65) Prior Publication Data

US 2015/0121592 P1 Apr. 30, 2015

(51) Int. Cl.
*A01H 5/02* (2006.01)

(52) U.S. Cl.
USPC ..... Plt./367

(58) Field of Classification Search
USPC ..... Plt./367
See application file for complete search history.

*Primary Examiner* — Anne Grunberg
(74) *Attorney, Agent, or Firm* — Jondle & Associates, P.C.

(57) ABSTRACT

A new and distinct variety of *Anthurium* plant named 'ANTHDINWAQ' particularly characterized by having durable rounded pink spathes that retain their color for a very long period of time, dark green durable glossy leaves, rich and early flowering throughout the year, rich shoot formation, a very compact and full plant habit and a plant height of 18 cm to 22 cm, is disclosed.

2 Drawing Sheets

Genus and species: *Anthurium andreanum* L.
Variety denomination: 'ANTHDINWAQ'.

BACKGROUND OF THE NEW PLANT

The present invention comprises a new and distinct variety of *Anthurium*, botanically known as *Anthurium andreanum* L., and hereinafter referred to by the variety name 'ANTHDINWAQ'. The new variety originated from a hybridization made in October 2004 in Bleiswijk, The Netherlands. The female parent is a purple-pink *Anthurium* pot plant named 'ANTHUCOEN' (U.S. Plant Pat. No. 22,630) and the male parent is a pink *Anthurium* plant named 'ANTHBESKA' (unpatented).

The new variety was selected in September 2006 from a selection of the hybridization and has been asexually reproduced repeatedly by tissue culture in Bleiswijk, The Netherlands over a five-year period. The present invention has been found to retain its distinctive characteristics through successive asexual propagations.

Plant Breeder's Rights for this variety have been applied for in Europe on Nov. 19, 2012. 'ANTHDINWAQ' has not been made publicly available or sold anywhere in the world more than one year prior to the filing of this application.

SUMMARY OF THE INVENTION

The following are the most outstanding and distinguishing characteristics of this new variety when grown under normal horticultural practices in Bleiswijk, The Netherlands.

1) A bright glossy pink colored small sized spathe;
2) Purple spadix;
3) Glossy leaves; and
4) Very compact plant habit.

DESCRIPTION OF THE PHOTOGRAPHS

This new *Anthurium* plant is illustrated by the accompanying photographs which show the overall plant habit including blooms, buds and foliage of the plant; the colors shown are as true as can be reasonably obtained by conventional photographic procedures. The photographs are of a 48-week old plant grown in a greenhouse in Bleiswijk, The Netherlands in 2012.

DESCRIPTION OF THE NEW VARIETY

Figure 1:
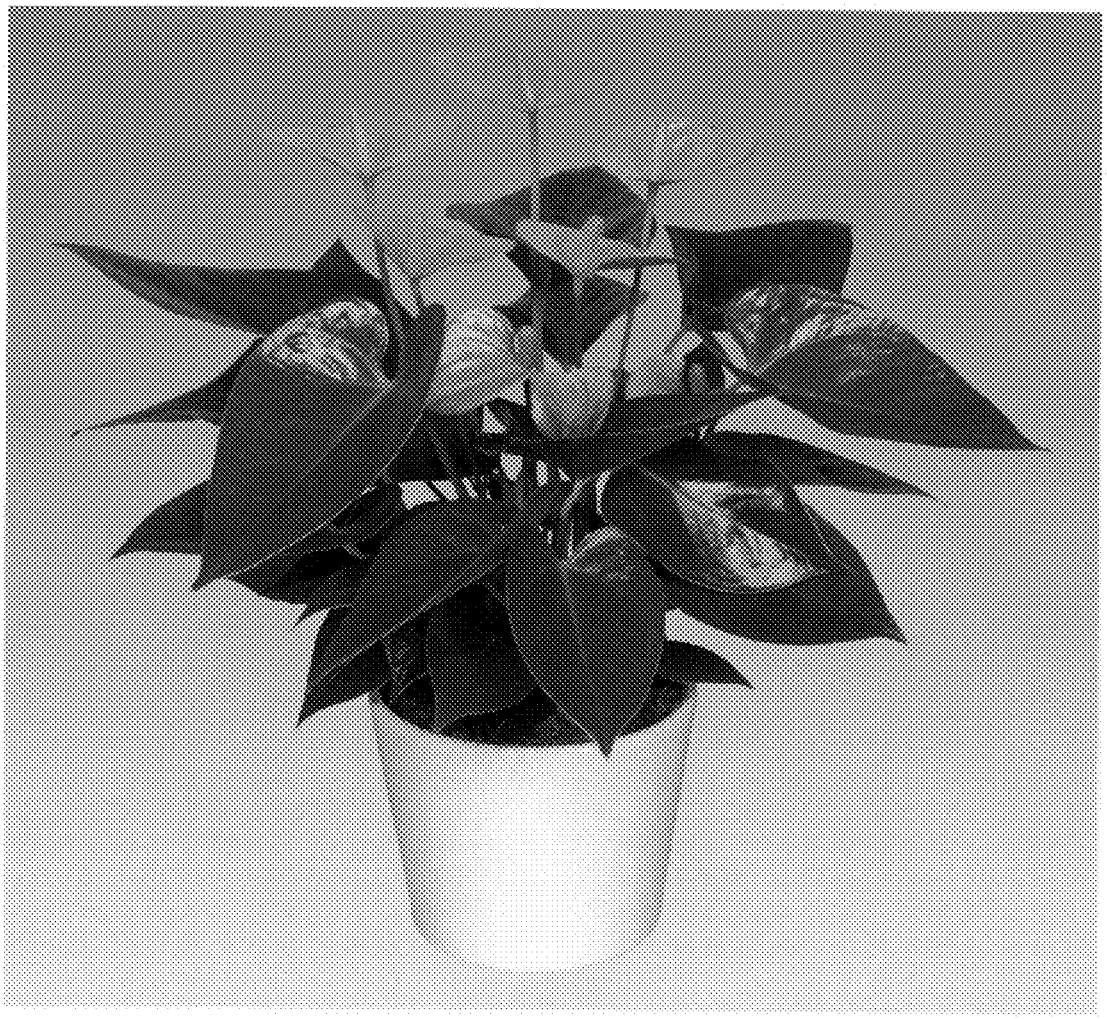
FIG. 1 shows the overall plant habit, including blooms, buds and foliage.
Figure 2:
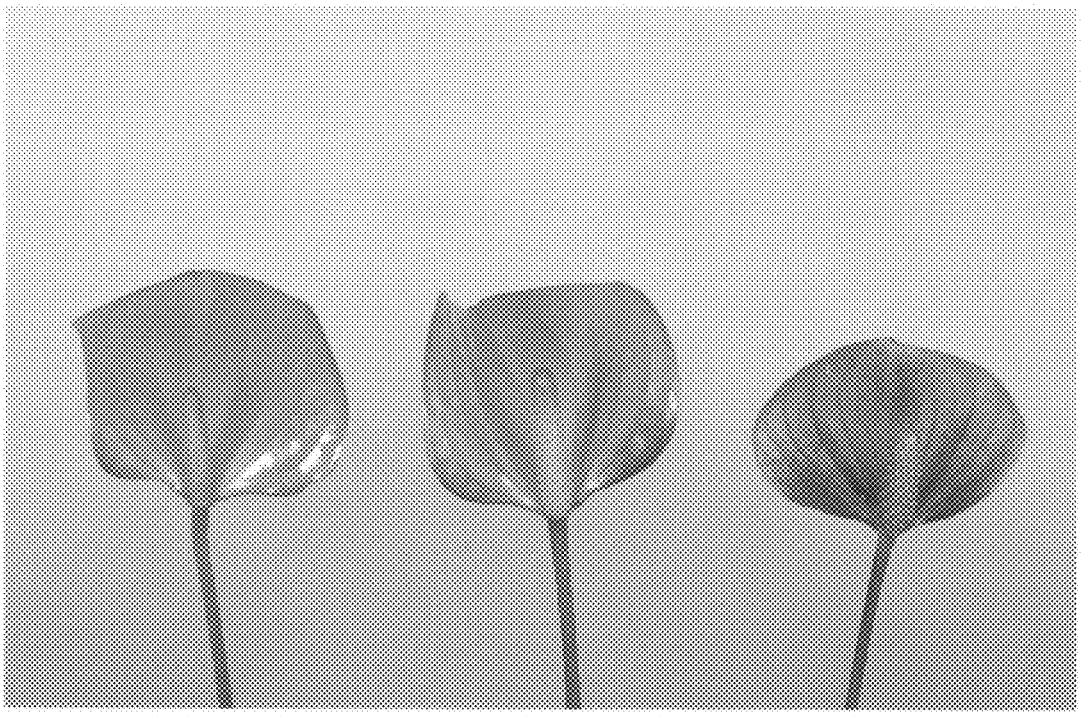
FIG. 2 shows the spathe in 3 ages.
Figure 3:
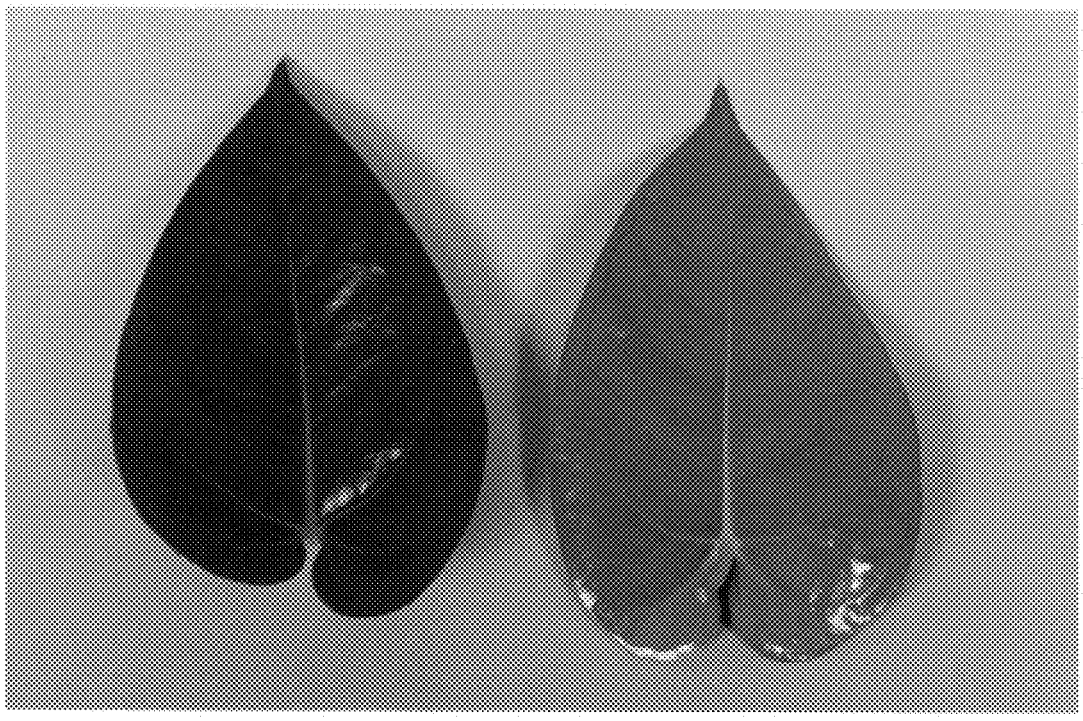
FIG. 3 shows the leaf from the underside (on the right) and the upperside (on the left).

The following detailed description sets forth the distinctive characteristics of 'ANTHDINWAQ'. The data which define these characteristics were collected from asexual reproductions carried out in Bleiswijk, The Netherlands. The plant history was taken on 48-week old plants which were planted from tissue culture in 12-cm pots and grown in a greenhouse between 19° C. and 24° C. Observations were made in February 2013. Color readings were taken under 5000 lux natural light in the greenhouse. Color references are primarily to The R.H.S. Colour Chart of The Royal Horticultural Society of London (R.H.S.) (2001).

DETAILED BOTANICAL DESCRIPTION

Classification:
*Family*.—Araceae.
*Botanical*.—*Anthurium andreanum* L.
*Common name*.—*Anthurium*.
*Denomination*.—'ANTHDINWAQ'.

Parentage:
*Female parent*.—*Anthurium* variety 'ANTHUCOEN' (U.S. Plant Pat. No. 22,630).
*Male parent*.—*Anthurium* variety 'ANTHBESKA' (unpatented).

Propagation:

*Propagation*.—Tissue culture.

*Root description*.—Fleshy cream roots with smaller hairy lateral roots; root-tips are yellow.

*Time to produce a finished flowering plant*.—45 to 50 weeks for a 12 cm pot.

Plant:

*Growth habit*.—Herbaceous perennial.

*Height* (*measured from soil, including inflorescence*).—18.0 cm to 22.0 cm.

*Width* (*measured from leaf tips*).—30.0 cm to 35.0 cm.

Leaves:

*Immature leaves*.—Length: 3.0 cm to 8.0 cm. Width: 2.0 cm to 5.0 cm. Color: Upper surface: RHS 139A (Green). Lower surface: RHS 137B (Green). Texture: Shiny (on both sides).

*Mature leaves*.—Length (fully expanded): 10.0 cm to 13.0 cm. Width: 6.0 cm to 9.0 cm. Shape: Ovate, weakly cupped. Apex: Acuminate. Base: Subcordate. Leaf blade angle with the petiole: Between 120 degrees and 150 Degrees. Leaf margin: Entire. Color: Upper surface: RHS 139A (Green). Lower surface: RHS 137C (Light green). Texture: Shiny, leathery and thick; non blistered (on both sides).

*Venation*.—Pinnate veining; the mid-vein and primary veins (the veins which radiate out from junction of petiole and leaf) protrude at the underside of the leaf blade.

*Venation color*.—Upper surface: RHS 137C (Green). Lower surface: RHS 147C (Light green).

*Lobes*.—Arrangement: Leaf blade has two big lobes extending past the Petiole. Length of lobes of mature leaf blades: 2.0 cm to 2.5 cm. Width of lobes of mature leaf blades: 3.0 cm to 4.0 cm. Distance from petiole/leaf junction to highest point on lobes of mature leaf blades: 2.0 cm to 3.0 cm.

*Petiole*.—Cross-section: Round. Diameter: 0.2 cm to 0.3 cm. Length: 9.0 cm to 11.0 cm for a mature leaf size. Color: Mature leaf: RHS 146C. Immature leaf: RHS 146B. Cataphyl color surrounding the petiole: Outside: RHS 146D (Light green). Inside: variable RHS 145C (Very pale green) to RHS 146D (Green).

*Geniculum*.—Length: 1.5 cm to 2.0 cm. Width: 0.3 cm to 0.4 cm. Colour: RHS 146C (Green).

Inflorescence:

*Arrangement*.—Solitary (Single).

*Flowering habit* (*length of flowering season*).—Continuous.

*Number of inflorescences per plant*.—6 to 12.

*Fragrance*.—Absent.

*Longevity of inflorescence on plant*.—More than a year.

*Longevity of the flower as a cutflower*.—Not observed.

Spathe:

*Buds*.—The spathe is tightly rolled around the spadix and extrudes from the peduncle sheath. After the spathe is fully opened the peduncle elongates some extra centimeters.

*Arrangement*.—Spathe angle with the peduncle is between 90 degrees and 110 degrees; the spathe stands on a wiry peduncle about 3 cm to 6 cm above the foliage.

*Shape*.—Rounded with a flat (non blistered) surface.

*Apex*.—Acute.

*Base*.—Obtuse.

*Texture*.—Shiny, non blistered (both sides).

*Margin*.—Entire.

*Size*.—Height: 11.0 cm to 16.0 cm (Peduncle length at maturity). Length: 4.0 cm to 6.0 cm. Width: 6.0 cm.

*Color*.—Just fully open: Upper surface: RHS 51A. Lower surface: RHS 51B. 7 to 8 weeks after opening: RHS 51A. 14 to 16 weeks after opening: The primary colour is between RHS 51B and RHS51C, depending on cultural conditions. The lobes accumulate very slowly some chlorophyll. The lobes become green (towards RHS 146A) very slowly.

Peduncle:

*Shape*.—Erect.

*Cross-section*.—Round.

*Length*.—11.0 cm to 16.0 cm.

*Diameter*.—0.2 cm to 0.3 cm.

*Color*.—RHS 146B (Green) at the base and just below the spathe some anthocyanins are present and colour is approximately RHS 182A.

Flowering time:

*General*.—One small rooted untreated tissue culture plant of 2 cm tall will flower, after 4 to 6 months 2 or 3 blossoms will appear, depending on the season. More blossoms appear after some additional weeks so that a full flowering and commercial plant will have 6 to 10 pink spathes. Smaller blossoms may occur on less mature growth.

Spadix:

*Size*.—Length: 1.5 cm to 2.5 cm (depending on flower size). Width (at apex): 0.3 cm to 0.5 cm. Width (at base): 0.4 cm to 0.6 cm.

*Shape*.—Columnar.

*Angle from spadixtip to peduncle*.—180 degrees (spadix is in one line with peduncle).

*Texture*.—When the spathe is unfurling the spadix is smooth. When the spadix matures, very small stigmata protrude. The stigmata are evenly distributed round the spadix. The spadix matures from base to top, slowly giving the spadix a bit rough appearance.

*Color*.—Immature: RHS 171A (Greyed-orange) to RHS 184C (Greyed-purple). Mature: RHS 77B (Purple). Ages to: RHS 182B (Brownish).

Flowers:

*Quantity per spadix*.—70 to 120.

*Spadix flower arrangement*.—Bisexual, rounded in cross-section.

*Shape*.—Rounded.

*Size*.—Length: 0.1 cm to 0.2 cm. Diameter (maximum): 0.2 cm.

*Color*.—RHS 77B (Purple).

Reproductive organs:

*Stamens*.—Not visible.

*Pollen*.—Very few or absent.

*Pollen color*.—Not measured.

*Pistil*.—Quantity: Many. Length: Less than 0.01 cm. Color: RHS 84C (Pale violet).

*Style*.—Not observed.

*Stigma*.—Shape: Ovoid. Diameter: Less than 0.01 cm. Color: RHS 77B (Purple).

*Ovary*.—Rarely visible.

*Ovary color*.—Not measured.

Fruit and seed set: Seed production has not been observed to date.

Disease and insect resistance: No particular resistance or susceptibility that is different from other *Anthurium* varieties.

COMPARISON WITH PARENTAL AND COMMERCIAL VARIETIES

'ANTHDINWAQ' differs from the female parent and commercial variety *Anthurium* 'ANTHUCOEN' (U.S. Plant Pat. No. 22,630), in that 'ANTHDINWAQ' has a pink spathe colour, whereas 'ANTHUCOEN' has a purple-pink spathe colour. Additionally, the spathes of 'ANTHUCOEN' are oblong, whereas the spathes of 'ANTHDINWAQ' are round.

'ANTHDINWAQ' differs from the male parent 'ANTHBESKA' (unpatented), by having a smaller spathe, leaves and overall plant habit.

'ANTHDINWAQ' can also be compared to commercial variety *Anthurium* 'Pink Champion' (U.S. Plant Pat. No. 12,115). Additional comparison data is shown in Table 1 below.

TABLE 1

Comparison of characteristics between 'ANTHDINWAQ', 'ANTHUCOEN' and 'Pink Champion'

| Characteristic | 'ANTHDINWAQ' | 'ANTHUCOEN' | 'Pink Champion' |
|---|---|---|---|
| Spathe colour | RHS 51A | RHS 186B | RHS 52B |
| Spadix colour | RHS 77B | RHS 84C | RHS 48B |
| Leaf length | 3-8 cm | 15-18 cm | 15-18 cm |
| Spathe blistering | Absent | Absent | Absent |
| Plant height at maturity | 18-22 cm | 35-45 cm | 40-50 cm |

I claim:

1. A new and distinct variety of *Anthurium* plant named 'ANTHDINWAQ' as illustrated and described herein.

* * * * *